United States Patent [19]

Tang

[11] Patent Number: 4,616,667
[45] Date of Patent: Oct. 14, 1986

[54] TOOTH CLEANING IMPLEMENT

[76] Inventor: I. Ping Tang, 606 Union Ave., Elizabeth, N.J. 07208

[21] Appl. No.: 542,765

[22] Filed: Oct. 17, 1983

[51] Int. Cl.$^4$ ............................................. A61C 15/00
[52] U.S. Cl. ...................................................... 132/89
[58] Field of Search .................... 132/89, 90, 93, 84 A, 132/DIG. 1; D28/64; D7/42

[56] References Cited

U.S. PATENT DOCUMENTS

| | | | |
|---|---|---|---|
| D. 172,481 | 4/1954 | Simmons | D28/64 |
| 194,447 | 8/1877 | Laurence | 132/90 |
| D. 199,832 | 12/1964 | Edelman et al. | D28/64 |
| 234,422 | 11/1880 | Osgood | 132/93 |
| D. 274,154 | 6/1984 | Bondurant | D28/64 |
| 516,409 | 3/1894 | Southwell | 132/89 |
| 590,280 | 9/1897 | Rockstroh | 132/90 |
| 710,498 | 10/1902 | McClain | 132/89 |
| 817,978 | 4/1906 | Lickman | 132/93 |
| 1,527,028 | 2/1925 | Daniel | 132/89 |
| 2,192,733 | 3/1940 | Bader, Jr. | 132/89 |
| 2,762,501 | 9/1956 | Cameron | 132/93 |
| 3,050,072 | 8/1962 | Diener | 132/93 |
| 3,605,765 | 10/1969 | Canby | 132/93 |
| 3,809,103 | 5/1974 | Bender | 132/93 |
| 3,910,293 | 10/1975 | Lemelson | 132/89 |
| 4,314,574 | 2/1982 | Inerte | 132/93 |

*Primary Examiner*—Robert Peshock
*Attorney, Agent, or Firm*—Jack B. Murray, Jr.

[57] ABSTRACT

An improved hand held dental instrument adapted for cleaning teeth is provided which, in its preferred form, comprises an elongated shaft and an angularly projected head, the head being provided with a longitudinal groove in the head's upper planar surface and being tapered so as to form a thin, flat tip suitable for deformation in a direction and manner to easily reach teeth crevices without sacrificing longitudinal rigidity of the head. The opposite end of this integrally formed device's shaft is provided with a second tapered tip, which may be similarly grooved, and is adapted for cleaning of tooth surfaces.

6 Claims, 11 Drawing Figures

TOOTH CLEANING IMPLEMENT

BACKGROUND OF THE INVENTION

1. Field of the Invention

This invention relates generally to instruments for cleaning teeth, and more specifically to tooth cleaning instruments which are adapted to remove food from between the inner surfaces of teeth, especially rear teeth.

2. Brief Description of the Prior Art

Conventional toothpicks are either wooden or plastic and are straight, thin elongated implements which taper almost to a point at one or both ends thereof. Food is removed from between teeth by directly thrusting one end of the toothpick into the tooth crevices, such as near the gums, and working the food outwardly and towards the ends of the teeth. In addition to suffering from the disadvantage of risking injury to the user's gums due to the need to thrust the toothpick end toward the gums during the cleaning operation, the conventional toothpicks are also disadvantaged by virtue of their design, which causes the angle of attack on rear tooth surfaces to decrease as the rearmost teeth are worked by the toothpick's end. The straight shaft and the pointed ends can only generally reach a portion of the rear crevices, and cannot efficiently remove food lodged between these remote surfaces.

Other toothpick and tooth cleaning instruments have been developed, but they all suffer disadvantages. Early tooth cleaning implements include those disclosed in U.S. Patents dating before 1900. U.S. Pat. No. 234,422 (1880) related to an instrument having a tooth cleaning portion formed as a thin metal blade provided with notches. U.S. Pat. No. 516,409 (1884) provided a pointed end formed from a piece of quill which was affixed to a shank portion by a longitudinal split in the adjacent end-portion of the shank. The instrument of U.S. Pat. No. 710,498 (1902) also employed a quill shaft and connected the quill to the point by means of an angled seat adapted to be fitted over the end of the quill shaft. U.S. Pat. No. 817,978 (1906) related to a single piece instrument having a semi-circular pointed hood at one end.

Design U.S. Pat. No. 172,481 (1954) also relates to a tooth cleaning instrument having a semi-circular hook portion at one end. Design U.S. Pat. No. 199,832 (1964) is drawn to the design of a toothpick device having a center shank portion and two angularly projected pick ends. Finally, U.S. Pat. No. 3,910,293 (1975) relates to a hand held tooth cleaning instrument provided with an elongated shaft and a rounded head portion at one end thereof, projecting outwardly from the shaft, and shaped to provide upper and lower edges and terminating in a tapered tip.

SUMMARY OF THE INVENTION

In accordance with the present invention, an improved hand held dental instrument adapted for the cleaning of teeth is provided which comprises an elongated shaft having an upper and lower end, the lower end of the shaft being provided with a first tapered portion which is tapered to a first tip; and a head portion integrally formed at the upper end of the shaft and extending outwardly therefrom. The head portion is suitably tapered to form a flat, thin second tip at the outer end of the head. Each of the first tapered portion and the head portion are provided with at least one planar surface, and at least one of these planar surfaces is provided with a longitudinal groove to increase the flexibility and tooth cleaning efficiency of the associated tip without substantially reducing the resistance of the associated planar surface from deformation along its longitudinal axis toward the shaft.

The dental implements of this invention provide greatly increased ease of removing food lodged between the surfaces of teeth, especially between surfaces of hard to reach rear teeth. The shaft is preferably of a substantially rectangular transverse cross-section to fascilitate placing and controlling the movement of either tip portion of the instrument. In addition, the longitudinally grooved cleaning tip permits deformation of the tip in such a manner and direction to reach in between the narrow gaps of teeth while not sacrificing the longitudinal rigidity of the cleaning tip which would otherwise limit the food removal efficiency of the device.

DETAILED DESCRIPTION OF THE INVENTION

Figure 4:
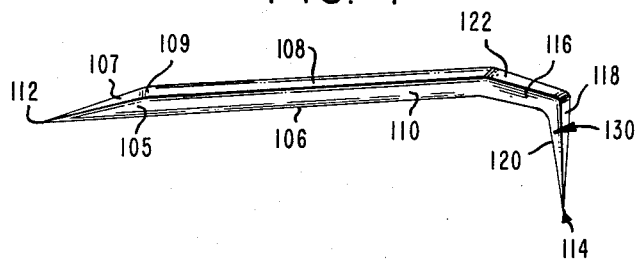
FIG. 4 is a perspective view of a second embodiment of the tooth cleaning instrument of this invention.
Figure 5:
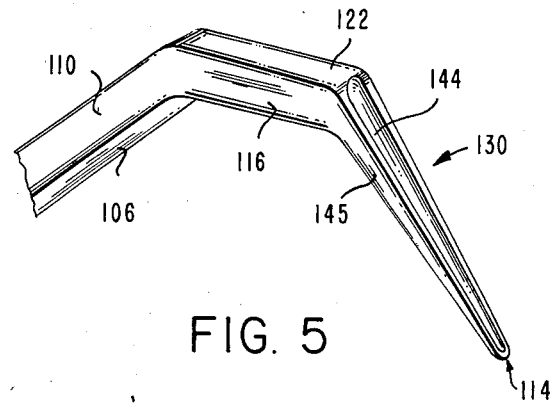
FIG. 5 is an enlarged, perspective view of head 130 and a portion of shaft 110 of the device of FIG. 4.
Figure 6:
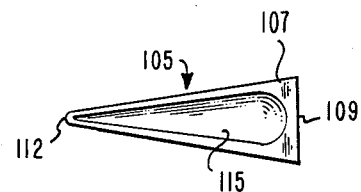
FIG. 6 is an end-on view of the first tapered portion 107 of the device of FIG. 4.
Figure 7:
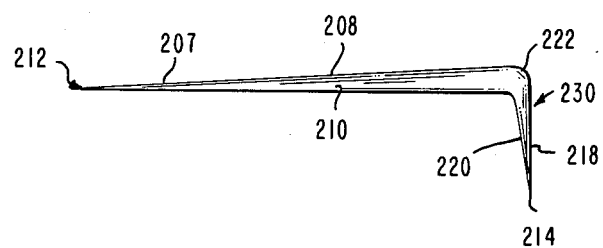
FIG. 7 is an elevational view of a third embodiment of the invention.
Figure 8:
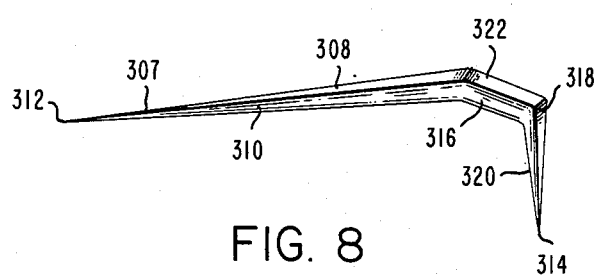
FIG. 8 is a perspective view of a fourth embodiment of the invention.

In the drawings, the same numbers refer to the same or similar elements, and the numeral "1" is added in FIGS. 4–6, and the numeral "2" is added in FIGS. 7 and 8, before the two digit numbers used in the remaining Figures in describing the same or similar elements of the latter group of Figures.

Referring to FIGS. 1, 2A, 2B and 3, the embodiment therein illustrated is provided with elongated shaft 10 having a substantially rectangular transverse cross-section and formed by upper planar surface 8, lower planar surface 6 and planar side walls 10. Alternatively, shaft 10 can be characterized by a substantially square cross-section or by a cross-sectional geometry which is formed by from three to eight sides. The shaft 10, when so formed, permits more precise control of the tooth cleaning surfaces of the instruments of this invention. Shaft 10 can also be formed so as to provide a substantially rounded or circular cross-section transversely, if desired.

At the lower portion of shaft 10 is a first tapered portion 7 which terminates in a first tip 12 and which is defined by side walls 5 and an upper planar surface 3. The lower planar surface of first tapered portion 7 is defined by a continuation of lower planar surface 6 of shaft 10. Upper planar surface 3 is formed to slope downwardly from the lower end 9 of shaft 10 to the first tip 12, and the side walls 5 are similarly tapered from lower end 9 of shaft 10 to tip 12. Within upper planar surface 3 is provided first longitudinal groove means 15 for providing the desired degree of flexibility to tip 12 and tapered portion 7, while at the same time minimizing the deformation of tapered portion 7 toward shaft 10 during use of tip 12 and permitting lower tapered portion 7 to function more efficiently in its cleaning function as will be explained in more detail below. Tip 12 and first tapered portion 7 are especially adapted to cleaning of surfaces of the front teeth.

Figure 1:
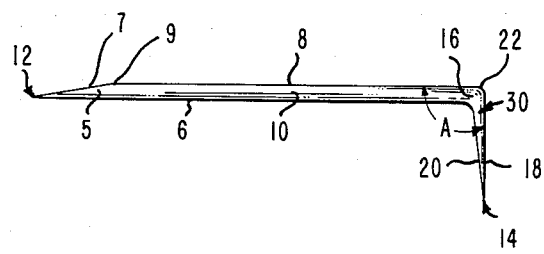
FIG. 1 is an elevational view of one embodiment of the tooth cleaning device of this invention.
Figure 2A:
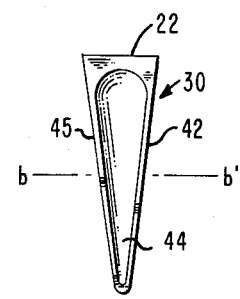
FIG. 2A is an enlarged, end-on view of the head portion of the device of FIG. 1.
Figure 3:
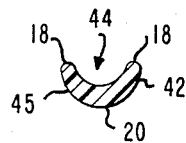
FIG. 3 is a cross-sectional view of the head portion shown in FIG. 2A, taken transversely along line b—b'.
Figure 2B:
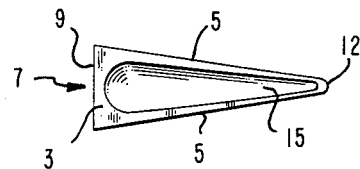
FIG. 2B is an enlarged, end-on view of the first tapered portion of the device of FIG. 1.

At the upper portion 22 of shaft 10 is provided an angularly projecting head 30 which extends outwardly from shaft 10 at an angle "A" of from about 70 to 135 degrees, preferably from about 80 to 100 degrees, and most preferably at substantially a right angle. As shown in FIG. 1, angle "A" is the interior angle of the intersection of the planes formed by upper planar surface 8 of shaft 10 and upper planar surface 18 of head 30. Head 30 is provided with upper planar surface 18, lower surface 20 and side walls 42 and 45. Side walls 42 and 45 and lower surface 20 preferably together form a continuously curved bottom surface as shown in FIG. 3, when head 30 is viewed transversely in cross-section, from upper portion 16 of head 30 downwardly to tip 14. Side wall 42 and 45 taper and lower surface 20 slopes inwardly toward upper planar surface 18, from the upper part 16 of head 30, downwardly to a tip 14, which is preferably flat and thin.

Head 30 is provided with a second longitudinal groove means 44 in upper surface 18 for imparting flexibility to enhance the tooth cleaning efficiency of head 30. As shown, means 44 comprises a groove which extends substantially the entire length of head 30. As with the groove 15 in first tapered portion 7, the function of groove 44 is to impart both improved stability and flexibility to head 30, permitting head 30 to be deformed in a variety of directions during use in cleaning teeth, without substantial compression of head 30 toward shaft 10 from tip 14, as will be explained in more detail below.

The dimensions and shape of grooves 15 and 44 can vary widely depending on such factors as the material of construction of the device, the dimensions of the respective surfaces in which the groove is positioned, the extent of tip flexibility desired and other factors. Generally, however, grooves 15 and 44 will occupy a substantial portion, preferably at least about 50%, and more preferably from about 75% to 95%, of the associated upper planar surfaces 3 and 18, respectively, and will taper downwardly to the associated tips 12 and 14, respectively. Similarly, the depth of grooves 15 and 44 can vary widely, but will generally range from about 10 to 80%, and preferably from about 30 to 60%, of the distance between upper planar surfaces 3 and 18 and the associated lower surfaces 6 and 20, as determined along the longitudinal axis of the respective tapered portion 7 and head 30. (It will be understood from the foregoing discussion that upper surfaces 3 and 18 are said herein to be "planar" even though the respective groove 15 or 44 is provided therein since the "rim" about the upper, outer periphery of the respective groove will lie in a substantially flat plane.)

The dimensions of shaft 10, head 30 and first tapered end portion 7 can also vary widely. Generally, however, shaft 10 will be from about 4 to 10 cm., and preferably from about 5 to 7 cm., long (as measured from the shaft's upper end 22 to its lower end 9), from about 2 to 4 mm. wide (i.e., the width of planar surfaces 6 and 8), and from about 1 to 3 mm. thick (i.e., the width of side walls 10). First tapered portion 7 and head 30 can each suitably be from about 0.75 to 2.5 cm. and preferably from about 1 to 2 cm., in length.

The function of the longitudinal grooves 15 and 44 in the associated cleaning end of the device of this invention (first tapered portion 7 and head 30, respectively) is to permit the tips 12 and 14 to bend or flex in any radial direction from the tip and to thereby impart enhanced cleaning motion in use of each tip, while maintaining sufficient rigidity to avoid substantial longitudinal compression or deformation of tapered portion 7 or head 30 from tips 12 or 14 toward shaft 10 and the upper portions 9 or 22 of the associated cleaning ends of the device. Preferably, first tapered portion 7 and head 30, and their associated grooves 15 and 44 are constructed such that, when the selected thin, flat and rounded tip 12 or 14 is inserted into the narrow crevice between adjacent teeth, the sections of the tapered portion 7 or head 30 adjoining the inserted tip are caused to undergo a flattening deformation by the compressive forces exerted thereon by the opposing surfaces of the adjacent teeth. For example, referring to FIGS. 2A and 3, when tip 14 of head 30 is inserted between adjacent teeth, upper planar surface 18 will be in contact with the outer surfaces of one of the teeth and lower surface 20 of head 30 will be in contact with the outer surfaces of the second tooth. As head 30 is forced deeper into the crevice, an increasing amount of compression force is exerted on the surfaces 18 and 20 by the adjacent teeth, causing the thus-inserted sections of head 30 to deform by flattening out (as viewed in transverse cross-section as in FIG. 3) in a manner and in an amount sufficient to react to the thus-applied compression forces. When the thus-inserted head 30 is moved in and out of the crevice, or up and down in the crevice, the pressure of surfaces 18 and 20 upon the opposing tooth surfaces enhances the tooth cleaning action of the device for removal of food lodged between these adjacent teeth. Furthermore, the thus-inserted head 30 can preferably conform to the irregularities in the contour of the adjacent tooth surfaces, thereby providing greatly improved cleaning action. Therefore, the device of this invention permits cleaning of teeth in a manner that is superior both to conventional toothpicks and to conventionally used dental floss.

Figure 9:
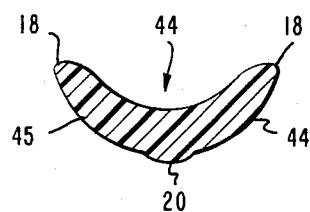
FIG. 9 is a transverse cross-sectional view of the head portion of another embodiment of the device of this invention, taken along b—b' as in FIG. 3.
Figure 10:
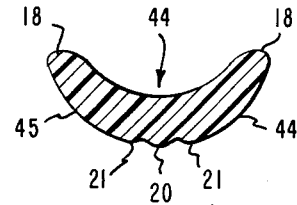
FIG. 10 is a transverse cross-sectional view of the head portion of yet another embodiment of the device of this invention, taken along line b—b' as in FIG. 3.

If desired, either lower surface 20 or upper planar surface 18 of head 30 can be formed to provide irregularities in their surface to increase the scraping action of the head 30. Thus, in FIGS. 9 and 10, head 30 is shown in alternative embodiments in which surface 20 is either provided with a rounded rib which is positioned along the length of head 30 (as shown in FIG. 9), or with longitudinal channels 21 along the length of head 30 (as shown in FIG. 10). Similar modifications can be made to the portion of lower surface 6 in first tapered portion 7, if desired.

Shaft 10, first tapered portion 7 and head 30 are preferably formed from a unitary material of construction, and can be molded (e.g., by injection molding) using high impact polystyrene resin, nylon resin, other thermoplastic materials having similar characteristic or thermosetting materials such as silicone rubber. The choice of material of construction and the manner in which the devices of this invention are made therefrom will be apparent to those having ordinary skill in the art, and a detailed discussion thereof is not essential to a full understanding of the present invention.

A second embodiment of the device of this invention is shown in FIGS. 3 and 4 which comprises shaft 110, first tapered portion 107, head 130 and angularly disposed member 116. As with the embodiment discussed above, first tapered portion 107 terminates in a tip 112, and shaft 110 is formed of substantially planar upper surface 108, planar lower surface 106, and planar side walls 110. At the upper portion of shaft 110 is provided angularly disposed member 116, which is also preferably formed of substantially planar sides and which links shaft 110 to head 130. Head 130 is also angularly disposed and projects outwardly from linking member 116, as well as from the extended plane formed by upper planar surface 108 of shaft 110. Preferably, linking shaft member 116 and head 130 are angularly disposed in such a manner at to provide head 130 in a position which essentially corresponds to the angular relationship of head 30 and shaft 10 in the embodiment of FIG. 1, as discussed above. Therefore, the angle of projection of member 116 from shaft 110 and of head 130 from member 116 is such that the plane of upper planar surface 118 would, if extended, intersect with the plane of upper planar surface 108, if extended, at an angle of from about 70 to 135 degrees, preferably from about 80 to 100 degrees, and most preferably at substantially 90 degrees.

Head 130 and upper planar surface 103 (not shown) of tapered portion 107 are each provided with a longitudinal groove means, with groove 144 in head 130 being illustrated as shown in FIG. 5. The dimensions, shape and relationships of the component parts of this embodiment of this invention are as described above for the embodiment of FIG. 1.

Third and fourth embodiments of the device of this invention are illustrated in FIGS. 7 and 8, wherein devices of FIGS. 1 and 4 are modified to comprise a shaft 210 (310) having a head 230 (330) at the upper end thereof and a tip 212 (312) at the lower end thereof. In the embodiments of FIGS. 7 and 8, the lower end of shaft 210 (310) does not have the beveled sloping, tapered end portion as shown in the previously illustrated and discussed embodiments. It will be understood that tips 212 and 312 can comprise a point, as in a conventional wooden toothpick, and in such a form will generally not be also provided with a longitudinal groove means as discussed above.

The foregoing detailed description has been given for the purposes of understanding only, and no unnecessary limitations should be understood therefrom, since some modifications will be apparent from the above description. For example, and not by way of limitation, it will be understood that head portions of this device, and tapered lower portions, can alone or in combination be provided with a longitudinal groove means in a planar surface thereof other than the ones which are illustrated, for example in the lower planar surfaces of such tooth cleaning ends. In each embodiment, the device of this invention is preferably provided with an angularly disposed head whose lower surface tapers to a tip at a rate which is less than the rate at which the sides of the head are tapered to the tip. This then provides the preferred flat, thin tip 14, 114, 214 and 314, respectively. Similarly by way of an additional modification to the foregoing, it will be apparent that the devices oF FIGS. 4 and 8 having angularly disposed shaft members 116 and 316, respectively, can be formed so that either linking member 116 (316), or head 130 (330), or both, lie in a plane which is above the plane formed by sidewalls 110 (310), thus forming a device having a "double offset". Thus, whereas the devices of FIGS. 4 and 8 each have components which lie in the same plane (that is, the plane of the paper if such devices were viewed in a non-perspective, elevational view), such modified "offset" devices would be characterized in such a non-perspective, elevational view by a linking member and/or head which lie outside the plane of the paper, either above or beneath the plane formed by the longitudinal shaft itself.

The improved tooth cleaning device of this invention therefore permits the cleaning of the gum line along and in between teeth, to remove food and prevent the formation of plaque, and accomplishes this result without the disadvantages of dental floss even though the device of this invention can be understood from the foregoing as being capable of use in a manner similar to conventional dental floss. These devices can be readily used by the consumer and can be fabricated inexpensively, if desired, so that the devices can be disposed of after one or more uses. Such toothpick devices of this invention, therefore, provide a highly efficient, convenient and inexpensive means of permitting the consumer to prevent the tooth and gum damage which can result from food deposits which are not removed, and thus furthers the important goal of sound dental hygiene.

I claim:

1. A dental instrument for cleaning teeth which comprises: an elongated shaft having an upper end and a lower end, said lower end being provided with a first tapered portion which is tapered to a first tip and which is provided with at least one planar surface thereon, said shaft additionally comprising a linking shaft member at the upper end of said shaft, said linking shaft member being angularly disposed from said shaft; and a head portion which is integrally joined to the upper end of said linking shaft member and which projects angularly therefrom, said head portion having at least one planar surface thereon and being tapered to a second tip, at least one of said planar surfaces in at least one of said first tapered portion and said head portion being further provided with longitudinal groove means for increasing the flexibility and tooth cleaning efficiency of the associated said tip, said first tapered portion and said head portion being each integrally formed from a material selected from the group consisting of a thermoplastic material and a thermosetting material said head portion, said linking shaft member and said shaft being in an angular relation to one another such that said head portion projects outwardly at an angle from 70 to 135 degrees relative to said shaft.

2. The dental instrument according to claim 1 wherein said shaft is characterized by a transverse cross-section having from three to eight sides.

3. The dental instrument according to claim 2 wherein said shaft is characterized by a substantially rectangular transverse cross-section.

4. The dental instrument according to claim 1 wherein said first and second tip are each characterized by having a flat, thin cross-section, and are each rounded, and wherein said planar surfaces of said first tapered portion and said head portion are each provided with longitudinal grooves which occupy at least about fifty percent of the area of said grooved planar surfaces.

5. The dental instrument according to claim 4 wherein each said groove is characterized at any point along said groove by a depth of from about 10 to 80% of the thickness of the associated said first tapered portion and said head portion, as determined at said point along said groove.

6. The dental instrument according to claim 1 wherein said angle is substantially a right angle, said shaft is characterized by a substantially rectangular transverse cross-section, and each of said first tapered portion and said head portion are provided with a substantially planar upper surface in which a longitudinal groove means for providing said flexibility is disposed.

* * * * *